United States Patent
Berndl et al.

(10) Patent No.: US 10,463,739 B2
(45) Date of Patent: Nov. 5, 2019

(54) SOLID RETARD FORMULATIONS BASED ON SOLID DISPERSIONS

(75) Inventors: Gunther Berndl, Bad Durkheim (DE); Juergen Weis, Frankfurt am Main (DE); Dietrich Granzow, Ludwigshafen (DE); Bernd Liepold, Dossenheim (DE); Ute Lander, Dannenfels (DE); Ulrich Westedt, Schriescheim (DE)

(73) Assignee: AbbVie Deutschland GmbH & Co. KG, Wiesbaden (DE)

( * ) Notice: Subject to any disclaimer, the term of this patent is extended or adjusted under 35 U.S.C. 154(b) by 389 days.

(21) Appl. No.: 13/993,066

(22) PCT Filed: Dec. 22, 2011

(86) PCT No.: PCT/EP2011/073850
§ 371 (c)(1),
(2), (4) Date: Dec. 27, 2013

(87) PCT Pub. No.: WO2012/085236
PCT Pub. Date: Jun. 28, 2012

(65) Prior Publication Data
US 2014/0296336 A1    Oct. 2, 2014

(30) Foreign Application Priority Data
Dec. 23, 2010 (EP) .................................. 10196936

(51) Int. Cl.
| | | |
|---|---|---|
| *A61K 47/34* | (2017.01) | |
| *A61K 9/14* | (2006.01) | |
| *A61K 9/20* | (2006.01) | |
| *A61K 9/00* | (2006.01) | |
| *A61K 31/167* | (2006.01) | |
| *A61K 31/192* | (2006.01) | |
| *A61K 31/216* | (2006.01) | |
| *A61K 47/32* | (2006.01) | |

(52) U.S. Cl.
CPC ................ *A61K 47/34* (2013.01); *A61K 9/00* (2013.01); *A61K 9/146* (2013.01); *A61K 9/2095* (2013.01); *A61K 31/167* (2013.01); *A61K 31/192* (2013.01); *A61K 31/216* (2013.01); *A61K 47/32* (2013.01); *A61K 9/2027* (2013.01); *A61K 9/2031* (2013.01)

(58) Field of Classification Search
CPC .. A61K 31/167; A61K 31/192; A61K 31/216; A61K 47/32; A61K 47/34; A61K 9/00; A61K 9/146; A61K 9/2027; A61K 9/2031; A61K 9/2095
See application file for complete search history.

(56) References Cited

U.S. PATENT DOCUMENTS

| | | |
|---|---|---|
| 4,769,236 A | 9/1988 | Panoz et al. |
| 4,801,460 A | 1/1989 | Goertz et al. |
| 4,880,585 A | 11/1989 | Klimesche et al. |
| 5,552,159 A | 9/1996 | Mueller et al. |
| 5,939,099 A | 8/1999 | Grabowski et al. |
| 9,205,027 B2 | 12/2015 | Kessler et al. |
| 2009/0011007 A1* | 1/2009 | Meier ................. A61K 9/1635 424/451 |
| 2009/0220596 A1* | 9/2009 | Rosenberg ......... A61K 31/4184 424/474 |
| 2012/0053248 A1 | 3/2012 | Kolter et al. |

FOREIGN PATENT DOCUMENTS

| | | |
|---|---|---|
| EP | 1832281 | 9/2007 |
| JP | 2009533320 | 9/2009 |
| WO | 01/34119 | 5/2001 |
| WO | 2007104748 | 9/2007 |
| WO | 2007/115381 | 10/2007 |
| WO | 2009/050289 A2 | 4/2009 |
| WO | 2010/000740 A1 | 1/2010 |
| WO | 2010/130728 A2 | 11/2010 |

OTHER PUBLICATIONS

Janssens, S. et al., "The use of a new hydrophilic polymer, Kollicoat IR, in the formulation of solid dispersions of Itraconazole," Eur. J. Pharm. Sci. (2007) 30:288-294.
Six, K. et al., "Increased physical stability and improved dissolution properties of Intraconazole, a class II drug, by solid dispersions that combine fast- and slow-dissolving polymers," J. Pharm. Sci. (2004) 93(1):124-131.
International Search Report, issued by the European Patent Office in International Patent Application No. PCT/EP2011/073850 (dated Apr. 18, 2012).
International Preliminary Report on Patentability, issued by the European Patent Office in International Patent Application No. PCT/EP2011/073850 (dated Jan. 11, 2013).
Serajuddin et al., "Solid dispersion of poorly water-soluble drugs: Early promises, subsequent problems, and recent breakthroughs," J. Pharm. Sci., 88 (10): 1058-1066 (1999) (Abstract).

* cited by examiner

*Primary Examiner* — Michael B. Pallay
(74) *Attorney, Agent, or Firm* — Neal, Gerber & Eisenberg LLP (57) ABSTRACT

A formulation comprising a melt-processed solid dispersion product comprising an active agent, a pharmaceutically acceptable thermoplastic polymer of N-vinyl lactams, and a pharmaceutically acceptable polyvinyl alcohol-polyalkylene glycol graft copolymer. A method for producing said formulation.

13 Claims, 3 Drawing Sheets

SOLID RETARD FORMULATIONS BASED ON SOLID DISPERSIONS

CROSS-REFERENCE TO RELATED APPLICATIONS

This is a U.S. national stage entry of International Patent Application No. PCT/EP2011/073850, filed on Dec. 22, 2011, which claims priority to European Patent Application No. 10196936.8, filed on Dec. 23, 2010, the contents of all of which are incorporated herein fully by reference.

FIELD OF THE INVENTION

The present invention relates to formulations comprising a melt-processed solid dispersion product, wherein an active agent is dispersed in a polymeric matrix; and methods for preparing such formulations.

Formulations produced by melt-processing to form a solid dispersion of an active agent such as a drug in a matrix of thermoplastic polymer(s) are generally known.

Melt extrusion of water-soluble polymers such as vinyl pyrrolidone copolymers or hydroxypropyl cellulose are described in European Patents EP 0240904 and EP 0240906.

The drug release characteristics of solid dispersions and their stability over time can be affected by the composition of the polymer matrix, wherein the drug is dispersed.

For example, EP 0 544 144 A1 describes pharmaceutical retard formulations produced by melt extrusion, wherein the polymer matrix comprises a mixture of water-soluble poly (meth)acrylates and water-insoluble hydroxypropyl cellulose. Such solid dispersion products are reported to retain their drug release characteristics over time, i.e. provide good storage stability, and to remain stable under mechanical stress, thus allowing regular drug release from tablets in the digestive tract Melt-processed solid dispersions with a polymer matrix comprising a mixture of water-soluble and water-insoluble cellulose derivatives are described in WO 96/25151. The ratio of this polymer mixture is reported to determine the drug release rate, thus allowing adjustment the retard effect when used in pharmaceutical formulations.

The freely soluble polyvinyl alcohol-polyethylene glycol graft copolymer Kollicoat IR is mainly used for the production of instant-release coatings for tablets.

WO 2007/115381 describes the use of polyvinyl alcohol-polyethylene glycol graft copolymers such as Kollicoat IR, namely for producing solid dispersions of drugs having a low aqueous solubility and dissolution rate such as itraconazole. Melt extrudates comprising 15, 20 or 25% itraconazole in a matrix of Kollicoat IR were reported to show a significantly faster drug release than physical mixtures comprising 20% glassy or crystalline itraconazole. However, a melt-extrudate comprising 40% itraconazole in Kollicoat IR was shown to comprise drug polymorphs, a separate glassy drug phase and a significantly slower drug release rate.

Janssens et al. (Eur J Pharm Sci 30:288-294, 2007) report that in solid dispersions of itraconazole in Kollicoat IR the polymer appears to be semi-crystalline, and that its crystallinity increased during the extrusion process due to exposure to heat and shear forces.

Six et al. (J Pharm Sci 93(1):124-131, 2004) describe solid dispersions prepared from itraconazole, the relatively slow dissolving polymer Eudragit E100 and the relatively fast dissolving polymer PVPVA64 that form a two-phase system and shown increased dissolution rates.

Pharmaceutical formulations comprising a water soluble carrier such as polyethylene glycol (PEG) and a crystallinization inhibitor such as polyvinylpyrolidone (PVP) or hydroxypropylcellulose (HPMC) are described in WO 01/34119.

As described above, there have been approaches to tailor the physicochemical properties of solid dispersion products by specific combinations of polymers. Nevertheless, there is a need to identify further polymer combinations that allow the preparation of solid dispersion products and a precise adjustment of the drug release rate of an active agent dispersed therein.

Although Kollicoat IR has been suggested as carrier in melt-processed solid dispersion products, in certain instances unacceptable levels of residual drug crystallinity have been observed. This would indicate that the dissolving power of Kollicoat IR for certain poorly soluble drugs is insufficient. Also, the high extrusion temperatures required for obtaining a homogeneous melt are undesirable.

Surprisingly, it has now been found that mixtures of polyvinyl alcohol-polyalkylene glycol graft copolymers such as Kollicoat IR and thermoplastic polymers of N-vinyl lactams can be used as matrix polymers for drug solid dispersions, wherein the drug release rate is adjustable through the ratio of said polymers.

SUMMARY OF THE INVENTION

Thus, the invention provides a formulation comprising a melt-processed solid dispersion product comprising, relative to the total weight of the solid dispersion product:
(a) one or more active agents;
(b) 10 to 90% (w/w) of at least one pharmaceutically acceptable thermoplastic polymer of N-vinyl lactams; and
(c) 5 to 60% (w/w) of at least one pharmaceutically acceptable polyvinyl alcohol-polyalkylene glycol graft copolymer.

The solid dispersion product comprises a matrix of the pharmaceutically acceptable polymers (b) and (c), wherein the active agent(s) is/are homogeneously distributed.

The matrix formed by the polymers (b) and (c) may be a homogenous mixture of said polymers which is chemically and physically uniform throughout or consists of only one phase (as defined in thermodynamics).

Alternatively, the mixture of polymers (b) and (c) may form a phase-separated or microphase-separated multicomponent system which comprises two or more phases which are immiscible with one another. Thus, one polymer may form domains which are interspersed in the other polymer, or two polymers form a co-continuous structure, wherein the individual polymers phases are intertwined and interlocked. In those cases where the polymers form two or more phases which are not miscible with one another the active agent can be present in the graft polymer phase or the thermoplastic polymer phase or both. The concentration of the active agent present in the individual phases is determined by its distribution coefficient.

The invention further provides a method for preparing the formulation described herein, the method comprising:
(a) preparing a homogenous melt from a mixture comprising one or more active agents; 10 to 90% (w/w) of at least one pharmaceutically acceptable thermoplastic polymer of N-vinyl lactams; and 5 to 60% (w/w) of at least one pharmaceutically acceptable polyvinyl alcohol-polyalkylene glycol graft copolymer; relative to the total weight of the mixture;

(b) forcing the thus obtained melt through one or more nozzles; and (c) allowing the melt to solidify to obtain a solid dispersion product.

DETAILED DESCRIPTION OF THE INVENTION

The term "pharmaceutically acceptable", as used herein, refers to a compound that does not cause acute toxicity when the formulation of the invention comprising it is administered in an amount that is required for medical or cosmetic treatment or medical prophylaxis, or that is taken up by consumption of the maximum recommended intake of a nutritional product comprising the formulation of the invention. Expediently, all components of the formulation of the present invention are pharmaceutically acceptable.

The pharmaceutically acceptable thermoplastic polymers used in the solid dispersion product described herein are polymers capable to act as a solid meltable solvent. They form a matrix for dispersion, and in particular for dissolution, of the active agent(s). Preferably, said polymers are at least partly soluble or swellable in aqueous media, expediently under the conditions of use, in particular under physiological conditions in the digestive tract if the formulation is intended for oral administration. Most preferably, said polymers are water-soluble polymers.

The pharmaceutically acceptable thermoplastic polymers of N-vinyl lactams may be selected from the group consisting of homopolymers and copolymers of N-vinyl pyrrolidone, e.g. polyvinylpyrrolidone (PVP), and copolymers of N-vinyl pyrrolidone and vinyl acetate or vinyl propionate, or mixtures of one or more thereof. Examples include copolymers of 60% (w/w) 1-vinyl-2-pyrrolidone and 40% (w/w) vinyl acetate such as Kollidon VA 64 (BASF), and 1-vinyl-2-pyrrolidone homopolymers such as Kollidon K17.

The term "graft copolymer" refers to a copolymer in which chains of a first polymer are grafted onto a second polymer chain. In other words, a graft copolymer has polymer chains of one kind "growing out" of the sides of polymer chains with a different chemical composition.

The pharmaceutically acceptable polyvinyl alcohol-polyalkylene glycol graft copolymer contained in the solid dispersion product described herein is a copolymer, wherein chains of a vinyl alcohol polymer grow out of the sides of polyalkylene glycol chains.

The graft copolymers are obtainable by grafting polyalkylene oxides with vinyl acetate, the graft copolymerization being initiated by free radicals. For this purpose, conventional polymerization initiators which decompose into free radicals under the polymerization conditions may be used. Alternatively, polymerization is initiated by high energy radiation.

One method of preparing the graft copolymers is to dissolve suitable polyalkylene oxides in vinyl acetate, add a polymerization initiator and carry out the polymerization continuously or batchwise. Another possible procedure is a semicontinuous one in which some, e.g. 10%, of the mixture to be polymerized, and consisting of polyalkylene oxide, vinyl acetate and initiator, is initially taken and heated to polymerization temperature and, after the polymerization has begun, the remainder of the mixture to be polymerized is added as the polymerization proceeds. The graft copolymers can also be obtained if the polyalkylene oxide is initially taken and heated to the polymerization temperature, and vinyl acetate and the initiator are added all at once, in batches or preferably continuously.

Hydrolysis of the graft copolymers, which leads to graft copolymers containing vinyl alcohol units, is carried out by adding a base, such as NaOH or KOH, or an acid, and, if required, heating the mixture. Polymers of this type are described in European Patent EP 0219048 and DE 10 77 430.

Polyethylene oxide having a number average molecular weight of from 2,000 to 100,000, in particular from 4,000 to 50,000, is preferably used as the grafting base. The weight ratio of polyalkylene glycol to vinyl alcohol polymer in said graft copolymer is usually in the range of from 1:0.2 to 1:10, preferably from 1:0.5 to 1:6. Up to 15% of the acetate groups of a vinyl acetate-polyalkylene glycol graft copolymer may be hydrolyzed. The polyvinyl alcohol-polyalkylene graft copolymer used according to the invention suitably have a K value according to Fikentscher of from 10 to 200, preferably from 20 to 100 (determined in a 1% strength by weight solution in ethyl acetate at 25° C.).

In one embodiment, the vinyl polymer chains of the polyvinyl alcohol-polyalkylene graft copolymer are polyvinyl alcohol chains with the general structure and the polyalkylene glycol chains have the general structure wherein Σn is from 250 to 1000, in particular 650 to 850; and m is from 100 to 500, in particular from 200 to 300. The symbol "n" indicates the number of repeating units of an individual polyvinyl alcohol chain and Σn is intended to mean the total number of vinyl alcohol repeating units per molecule of polyvinyl alcohol-polyalkylene graft copolymer.

Preferred polyvinyl alcohol-polyethylene glycol graft copolymers, e.g. Kollicoat IR (available from BASF AG, Ludwigshafen, Germany), are composed of about 75% (w/w) polyvinyl alcohol (PVA) units and about 25% (w/w) polyethylene glycol (PEG) units, and optionally 0.3% (w/w) colloidal silica which may improve the flow properties of the graft copolymer. Such polyvinyl alcohol-polyethylene glycol graft copolymers include those having a viscosity of from about 90 mPa·s to about 140 mPa·s, in particular of about 115 mPa·s, in a 20% (w/w) aqueous solution; and those with a number average molecular weight of approximately 45,000 Daltons.

In one embodiment of the invention, the weight ratio of the polyvinyl alcohol-polyalkylene glycol graft copolymer(s) to the thermoplastic polymer(s) of N-vinyl lactams is from about 1:1 to about 1:8, in particular from about 1:2 to about 1:5.

The solid dispersion product described herein may comprise about 1 to up to 60% (w/w), for example up to 40% (w/w), up to 30% (w/w), up to 20% (w/w), or about 1 to about 10% (w/w), of the one or more active agent(s) relative to the total weight of the product.

In particular, the active agent(s) comprised in solid dispersion product described herein may be selected from the group comprising pharmaceutically active agents, cosmetically active agents and nutritional supplements. The invention is particularly useful for water-insoluble or poorly water-soluble (or "lipophilic") compounds. Compounds are considered water-insoluble or poorly water-soluble when their solubility in water at 25° C. is less than 1 g/100 ml.

Examples of suitable pharmaceutically active ingredients include, but are not limited to:

analgesics and anti-inflammatory drugs such as fentanyl, indomethacin, ibuprofen, naproxene, diclofenac, diclofenac sodium, fenoprofen, acetylsalicylic acid, ketoprofen, nabumetone, paracetamol, piroxicam, meloxicam, tramadol, and COX-2 inhibitors such as celecoxib and rofecoxib;

anti-arrhythmic drugs such as procainamide, quinidine and verapamil;

antibacterial and antiprotozoal agents such as amoxicillin, ampicillin, benzathine penicillin, benzylpenicillin, cefaclor, cefadroxil, cefprozil, cefuroxime axetil, cephalexin, chloramphenicol, chloroquine, ciprofloxacin, clarithromycin, clavulanic acid, clindamycin, doxyxycline, erythromycin, flucloxacillin sodium, halofantrine, isoniazid, kanamycin sulphate, lincomycin, mefloquine, minocycline, nafcillin sodium, nalidixic acid, neomycin, nortloxacin, ofloxacin, oxacillin, phenoxymethyl-penicillin potassium, pyrimethamine-sulfadoxime and streptomycin;

anti-coagulants such as warfarin;

antidepressants such as amitriptyline, amoxapine, butriptyline, clomipramine, desipramine, dothiepin, doxepin, fluoxetine, reboxetine, aminepetine, selegiline, gepirone, imipramine, lithium carbonate, mianserin, milnacipran, nortriptyline, paroxetine, sertraline and 3-[2-[3,4-dihydrobenzofuro[3,2-c]pyridin-2(1H)-yl]ethyl]-2-methyl-4H-pyrido[1,2-a]pyrimidin-4-one;

anti-diabetic drugs such as glibenclamide and metformin;

anti-epileptic drugs such as carbamazepine, clonazepam, ethosuximide, gabapentin, lamotrigine, levetiracetam, phenobarbitone, phenytoin, primidone, tiagabine, topiramate, valpromide and vigabatrin;

antifungal agents such as amphotericin, clotrimazole, econazole, fluconazole, flucytosine, griseofulvin, itraconazole, ketoconazole, miconazole nitrate, nystatin, terbinafine and voriconazole;

antihistamines such as astemizole, cinnarizine, cyproheptadine, decarboethoxyloratadine, fexofenadine, flunarizine, levocabastine, loratadine, norastemizole, oxatomide, promethazine and terfenadine;

anti-hypertensive drugs such as captopril, enalapril, ketanserin, lisinopril, minoxidil, prazosin, ramipril, reserpine, terazosin and telmisartan;

anti-muscarinic agents such as atropine sulphate and hyoscine;

antineoplastic agents and antimetabolites such as platinum compounds, such as cisplatin and carboplatin; taxanes such as paclitaxel and docetaxel; tecans such as camptothecin, irinotecan and topotecan; vinca alkaloids such as vinblastine, vindecine, vincristine and vinorelbine; nucleoside derivatives and folic acid antagonists such as 5-fluorouracil, capecitabine, gemcitabine, mercaptopurine, thioguanine, cladribine and methotrexate; alkylating agents such as the nitrogen mustards, e.g. cyclophosphamide, chlorambucil, chlormethine, iphosphamide, melphalan, or the nitrosoureas, e.g. carmustine, lomustine, or other alkylating agents, e.g. busulphan, dacarbazine, procarbazine, thiotepa; antibiotics such as daunorubicin, doxorubicin, idarubicin, epirubicin, bleomycin, dactinomycin and mitomycin; HER 2 antibodies such as trastuzumab; podophyllotoxin derivatives such as etoposide and teniposide; famesyl transferase inhibitors; anthrachinon derivatives such as mitoxantron;

anti-migraine drugs such as alniditan, naratriptan and sumatriptan;

anti-Parkinsonian drugs such as bromocryptine mesylate, levodopa and selegiline;

antipsychotic, hypnotic and sedating agents such as alprazolam, buspirone, chlordiazepoxide, chlorpromazine, clozapine, diazepam, flupenthixol, fluphenazine, flurazepam, 9-hydroxyrisperidone, lorazepam, mazapertine, olanzapine, oxazepam, pimozide, pipamperone, piracetam, promazine, risperidone, selfotel, seroquel, sertindole, sulpiride, temazepam, thiothixene, triazolam, trifluperidol, ziprasidone and zolpidem;

anti-stroke agents such as lubeluzole, lubeluzole oxide, riluzole, aptiganel, eliprodil and remacemide;

antitussives such as dextromethorphan and laevodropropizine;

antivirals such as acyclovir, ganciclovir, loviride, tivirapine, zidovudine, lamivudine, zidovudine/lamivudine, didanosine, zalcitabine, stavudine, abacavir, lopinavir, amprenavir, nevirapine, efavirenz, delavirdine, indinavir, nelfinavir, ritonavir, saquinavir, adefovir and hydroxyurea;

beta-adrenoceptor blocking agents such as atenolol, carvedilol, metoprolol, nebivolol and propanolol;

cardiac inotropic agents such as amrinone, digitoxin, digoxin and milrinone;

corticosteroids such as beclomethasone dipropionate, betamethasone, budesonide, dexamethasone, hydrocortisone, methylprednisolone, prednisolone, prednisone and triamcinolone;

disinfectants such as chlorhexidine;

diuretics such as acetazolamide, furosemide, hydrochlorothiazide and isosorbide;

enzymes;

gastro-intestinal agents such as cimetidine, cisapride, clebopride, diphenoxylate, domperidone, famotidine, lansoprazole, loperamide, loperamide oxide, mesalazine, metoclopramide, mosapride, nizatidine, norcisapride, olsalazine, omeprazole, pantoprazole, perprazole, prucalopride, rabeprazole, ranitidine, ridogrel and sulphasalazine;

haemostatics such as aminocaproic acid;

HIV protease inhibiting compounds such as ritonavir, lopinavir, indinavir, saquinavir, 5(S)-Boc-amino-4(S)-hydroxy-6-phenyl-2(R)phenylmethylhexanoyl-(L)-Val-(L)-Phe-morpholin-4-ylamide, 1-Naphthoxyacetyl-beta-methylthio-Ala-(2S,3S)3-amino-2-hydroxy-4-butanoyl 1,3-thiazolidine-4-t-butylamide, 5-isoquinolinoxyacetyl-beta-methylthio-Ala-(2S,3S)-3-amino-2-hydroxy-4-butanoyl-1,3-thiazolidine-4-t-butylamide, [1S-[1R—(R—),2S*)—N'-[3-[[[(1,1-dimethylethyl)amino]carbonyl](2-methylpropyl)amino]-2hydroxy-1-(phenylmethyl)propyl]-2-[(2-quinolinylcarbonyl)amino]-butanediamide, amprenavir; DMP-323; DMP-450; nelfinavir, atazanavir, tipranavir, palinavir, darunavir, RO033-4649, fosamprenavir, P-1946, BMS 186,318, SC-55389a; BILA 1906 BS, tipranavir;

lipid regulating agents such as atorvastatin, fenofibrate, fenofibric acid, lovastatin, pravastatin, probucol and simvastatin;

local anaesthetics such as benzocaine and lignocaine;

opioid analgesics such as buprenorphine, codeine, dextromoramide, dihydrocodeine, hydrocodone, oxycodone and morphine;

parasympathomimetics and anti-dementia drugs such as AIT-082, eptastigmine, galanthamine, metrifonate, milameline, neostigmine, physostigmine, tacrine, donepezil, rivastigmine, sabcomeline, talsaclidine, xanomeline, memantine and lazabemide;

peptides and proteins such as antibodies, becaplermin, cyclosporine, tacrolimus, erythropoietin, immunoglobulins and insuline;

sex hormones such as oestrogens: conjugated oestrogens, ethinyloestradiol, mestranol, oestradiol, oestriol, oestrone; progestogens; chlormadinone acetate, cyproterone acetate, 17-deacetyl norgestimate, desogestrel, dienogest, dydrogesterone, ethynodiol diacetate, gestodene, 3-keto desogestrel, levonorgestrel, lynestrenol, medroxyprogesterone acetate, megestrol, norethindrone, norethindrone acetate, norethisterone, norethisterone acetate, norethynodrel, norgestimate, norgestrel, norgestrienone, progesterone and quingestanol acetate;

stimulating agents such as sildenafil, vardenafil;

vasodilators such as amlodipine, buflomedil, amyl nitrite, diltiazem, dipyridamole, glyceryl trinitrate, isosorbide dinitrate, lidoflazine, molsidomine, nicardipine, nifedipine, oxpentifylline and pentaerythritol tetranitrate;

their N-oxides, their pharmaceutically acceptable acid or base addition salts, their hydrates, their solvates, their stereochemically isomeric forms, and their polymorphs.

Pharmaceutically acceptable acid addition salts comprise the acid addition salt forms which can be conveniently obtained by treating the base form of the active ingredient with appropriate organic and inorganic acids.

Active ingredients containing an acidic proton may be converted into their non-toxic metal or amine addition salt forms by treatment with appropriate organic and inorganic bases.

The term "addition salt" also comprises the hydrates and solvent addition forms which the active ingredients are able to form. Examples of such forms are hydrates, alcoholates and the like.

The N-oxide forms of the active ingredients comprise those active ingredients in which one or several nitrogen atoms are oxidized to the so-called N-oxide.

The term "stereochemically isomeric forms" defines all possible stereoisomeric forms which the active ingredients may possess. In particular, stereogenic centers may have the R- or S-configuration and active ingredients containing one or more double bonds may have the E- or Z-configuration.

The solid dispersion product described herein may further comprise at least one plasticizer, e.g., 5 to 20% (w/w) of at least one plasticizer.

As used herein, the term "plasticizer" includes all compounds capable of plasticizing the polymers contained in solid dispersion product. The plasticizer should be able to lower the glass transition temperature or softening point of the polymer(s), in order to allow for lower processing temperature, extruder torque and pressure during the hot-melt extrusion process. Plasticizers also generally reduce the viscosity of a polymer melt thereby allowing for lower processing temperature and extruder torque during hot-melt extrusion.

Plasticizers useful in the invention include, by way of example and without limitation, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, and poly(ethylene glycol).

Such plasticizers may be ethylene glycol, propylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, triethyl citrate, acetyl triethyl citrate, tributyl citrate and allyl glycolate. All such plasticizers are commercially available from sources such as Aldrich or Sigma Chemical Co.

The PEG based plasticizers are available commercially or may be made by a variety of methods, such as disclosed in Poly (ethylene glycol) Chemistry: Biotechnical and Biomedical Applications (J. M. Harris, Ed.; Plenum Press, NY) the teachings of which are hereby incorporated by reference. Examples include polyethylene glycols having a number average molecular weight of from 600 to 6,000 Daltons, in particular from 1,000 to 2,000 Daltons.

The amount of plasticizer used in the formulation will depend upon its composition, physical properties, effect upon the polymer to be plasticized, interaction with other components of the formulation, ability to solubilize the therapeutic compound or other factors to be considered in the preparation of pharmaceutical formulations. The amount of plasticizer present in the formulation affects its properties. By way of example, when the plasticizer is PEG, its content will generally not exceed about 40% (w/w) of the formulation.

Various additives may be included in the formulation of the invention, for example lubricants, fillers, disintegrants, preservatives or stabilizers such as antioxidants, light stabilizers, radical scavengers and stabilizers against microbial attack, dyes such as azo dyes, organic or inorganic pigments such as iron oxides or titanium dioxide, or dyes of natural origin, pH regulators, as well as compounds which alter or mask flavor and/or odor of the formulation such as sweeteners, flavorings and odorants.

The matrix of the solid dispersion product is formed by the polyvinyl alcohol-polyalkylene glycol graft copolymer(s); the thermoplastic polymer(s) of N-vinyl lactams; and the optionally present plasticizer. It is particularly preferred that the active agent(s) in the solid dispersion product is/are present in an essentially non-crystalline state. This encompasses a state wherein essentially amorphous domains of active agent(s) are interspersed in the matrix, and a state wherein the active agent(s) are molecularly dispersed in the matrix or, where the matrix is composed of a phase-separated multicomponent system, in at least one of the polymer phases constituting the multicomponent system. When said dispersion of the active agent(s) in the polymer phase is such that the system of active agent and polymer is chemically and physically uniform or homogeneous throughout, such a solid dispersion will be called a "solid solution" or a "molecular dispersion". The state of molecular dispersion corresponds to the maximum possible homogenization of the active agent in the polymer phase.

Known analytical methods can be used to investigate the state of such solid dispersions, for example differential scanning calorimetry (DSC) or wide angle X-ray scattering measurements (WAXS measurements). The DSC analytical measurement of an essentially non-crystalline state lacks the melting peak which occurs with the crystalline pure substance and is usually endothermic. Another possibility for identifying an essentially non-crystalline state is the reduction in intensity and/or absence of typical X-ray diffraction signals in the WAXS analysis.

The solid dispersion product can be produced by blending one or more active agents, one or more pharmaceutically acceptable thermoplastic polymer(s) of N-vinyl lactams, as well as one or more pharmaceutically acceptable polyvinyl alcohol-polyalkylene glycol graft copolymer(s); heating the blend to obtain a homogeneous melt; and allowing the melt to solidify to obtain a solid dispersion product. The terms "melt" and "melting" should be interpreted broadly. For the purposes herein, these terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt, thus forming a solution, which, upon cooling, may form a solid dispersion having advantageous dissolution properties. Blending and heating are conveniently performed in a mixer or kneader which is jacketed for heating.

A preferred method for producing the formulation of present invention comprises:
(a) blending one or more active agents; 10 to 90% (w/w) of at least one pharmaceutically acceptable thermoplastic polymer of N-vinyl lactams; and 5 to 60% (w/w) of at least one pharmaceutically acceptable polyvinyl alcohol-polyalkylene glycol graft copolymer; relative to the total weight of the mixture;
(b) heating the blend to obtain a homogeneous melt;
(c) forcing the thus obtained melt through one or more nozzles; and
(d) allowing the melt to solidify to obtain a solid dispersion product.

Steps a) to c) may be performed in one or more than one apparatus suitable for this purpose, such as an extruder or kneader extruder. Preferably, the blend is subjected to a mixing action in a mixing section of the extruder.

Extruders are known per se. An extruder comprises a housing or barrel divided into several sections in a longitudinal direction. On the upstream side of the extruder, an opening is provided for feeding the active agent(s), pharmaceutically acceptable thermoplastic polymer(s) of N-vinyl lactams, the pharmaceutically acceptable polyvinyl alcohol-polyalkylene glycol graft copolymer(s), and any further components such as the plasticizer(s) and/or additives described herein. Usually, a hopper is placed on this opening so that the ingredients, usually in the form of powders, can be easily fed into the barrel of the extruder. The barrel ends in conveying direction in a die, where the dispersion is expelled.

The extruder comprises at least one rotating shaft. Alternatively, it may comprise two or up to six rotating shafts. The shafts may be co-rotating or counter-rotating. Processing elements disposed on adjacent shafts closely intermesh.

Each shaft carries a plurality of processing elements disposed axially one behind the other. The processing elements define a feeding and conveying section, at least one mixing section, and a discharging section. The feeding and conveying section is positioned farthest upstream, close to the hopper of the extruder, the at least one mixing section is positioned downstream of the feeding and conveying section, and the discharging section is positioned farthest downstream, close to the discharge opening of the extruder. The term "downstream" as used herein, refers to direction in which the material is being conveyed in the extruder, i.e. the conveying direction.

The processing elements of the feeding and conveying section as well as the discharging section are formed by screw-type elements. Preferably, these screw type elements form an endless screw having the feed direction and a uniform pitch flight. Thus, in the feeding and conveying section the powder is fed into the extruder and conveyed in the downstream direction, for example at a feed rate of 0.5 to 1.5 h or 0.5 to 1.0 kg/h.

In the mixing section(s) the material to be processed is homogenized by mixing or kneading. Paddle means or kneading blocks have conventionally been employed in kneading and plasticizing pharmaceutical mixtures. These kneading blocks consist of cam disks mutually offset at an angle in a peripheral direction. The cam disks have abutting faces that are perpendicular to the general conveying direction in the extruder. Alternatively, the mixing section(s) are defined by processing element(s) that comprise(s) a mixing element that is derived from a screw type element. A mixing element "being derived from a screw type element" is intended to mean an element whose basic shape is that of a screw element, but which has been modified such that it exerts a compounding or mixing effect in addition to a conveying effect. The underlying screw type element may have a positive-flight (positive-feed, "right-handed") screw element, may have a reverse-flight (negative-feed, "left-handed") screw element or a combination thereof. A preferred mixing element has a plurality of concentric ring portions formed by grooves turned into a screw type element. Therefore, the mixing element has a continuous screw flight, which is interrupted only by turned grooves with ring portions. Advantageously, the mixing element comprises screw portions between the ring portions which first cause a pressure buildup that forces the substance through the annular gap between the extruder housing and the ring portions with shearing action and elongation; the pressure is then reduced again.

The extruder shaft may further comprise one or more than one reverse-flight section(s), preferably arranged after the (last) mixing section and defined by reverse-flight elements. A reverse-flight element has a screw with a reverse-flight relative to the screw-type elements which may be arranged in the feeding and conveying section which define the general conveying direction of the extruder. Thus, the reverse-flight element convey the material in an opposite direction relative to the general conveying direction of the extruder and serves to create sufficient back-pressure to allow for a desired degree of mixing and/or homogenization. The reverse-flight element is designed to stow the material conveyed in the extruder. Therefore it may also be called a back-pressure element.

The substances which are fed to the extruder are melted in order to homogenize the melt and to disperse or, preferably, dissolve the active agent in the matrix efficiently. "Melting" means transition into a liquid or rubbery state in which it is possible for one component to be homogeneously embedded in the other. Melting usually involves heating above the softening point of the polymer. Usually, the maximum melt temperature is in the range of from 70 to 200° C., for example from 110 to 190° C., preferably not more than 160° C., e.g. not more than 140° C.

The extruder housing is heated in order to form a melt from the substances fed to the extruder. It will be appreciated that the working temperatures will also be determined by the kind of extruder or the kind of configuration within the extruder that is used. A part of the energy needed to melt, mix and dissolve the components in the extruder can be provided by heating elements, while the friction and shearing of the material in the extruder can also provide the mixture with a substantial amount of energy and aid in the formation of a homogeneous melt of the components.

In order to obtain a homogeneous distribution and a sufficient degree of dispersion of the active agent, the melt is kept in the heated barrel of the melt extruder for a sufficient length of time.

The extrudate exiting from the extruder ranges from pasty to viscous. Before allowing the extrudate to solidify, the extrudate may be directly shaped into virtually any desired shape. Shaping of the extrudate may be conveniently carried out by a calender with two counter-rotating rollers with mutually matching depressions on their surface. A broad range of tablet forms can be attained by using rollers with different forms of depressions. If the rollers do not have depressions on their surface, films can be obtained. Alternatively, the extrudate is moulded into the desired shape by injection-moulding. Alternatively, the extrudate is subjected to profile extrusion and cut into pieces, either before (hot-cut) or after solidification (cold-cut).

Optionally, the solid dispersion product resulting from such process of melt extrusion is milled or ground to granules. The granules may then be compacted. Compacting means a process whereby a powder mass comprising the granules is condensed under high pressure in order to obtain a compact with low porosity, e.g. a tablet. Compression of the powder mass is usually done in a tablet press, more specifically in a steel die between two moving punches.

For oral administration of the formulations of the invention a variety of dosage forms may be used comprising liquid or semisolid forms such as emulsions, microemulsions and suspensions, and solid forms such as granules, capsules, pellets, powders or tablets.

Emulsions and microemulsions may be of the oil-in-water or water-in-oil type and contain formulations of the invention as disperse or dispersing phase. These emulsions or microemulsions may be stabilized by the presence of emulsifiers known to be used for this purpose.

Granules consist of solid grains of formulations of the invention, each grain representing an agglomerate of powder particles. A lubricant is preferably used in compacting the granules. Suitable lubricants are selected from polyethylene glycol (e.g., having a Mw of from 1,000 to 6,000), magnesium and calcium stearates, sodium stearyl fumarate, and the like. The user can be offered single-dose preparations, for example granules packed in a small bag (sachet), a paper bag or a small bottle, or multidose preparations which require appropriate dimensions. However, in many cases, such granules do not represent the actual drug form, but are intermediates in the manufacture of particular drug forms, for example tablet granules to be compressed to tablets, capsule granules to be packed into hard gelatin capsules, or instant granules or granules for oral suspension to be put in water before intake.

As capsules, the formulations of the invention are usually packed into a hard shell composed of two pieces fitted together or a soft, one-piece, closed shell, which may vary in shape and size. It is likewise possible for formulations of the invention to be encased or enveloped or embedded in a matrix in suitable polymers, i.e. microcapsules and microspherules. Hard and soft capsules consist mainly of gelatin, while the latter have a suitable content of plasticizing substances such as glycerol or sorbitol. Hard gelatin capsules are used to receive formulations of the invention which have a solid consistency, for example granules, powder or pellets. Soft gelatin capsules are particularly suitable for formulations with a semisolid consistency and, if required, also viscous liquid consistency.

Pellets are granules of formulations of the invention in the particle size range from about 0.5 to 2 mm in diameter. Both with a narrow particle size distribution, preferably from 0.8 to 1.2 mm, and with an essentially round shape, are preferred.

Tablets are solid preparations in particular for oral use. The meaning of "oral administration" within the framework of the present invention is, in particular, that of the term "peroral administration" or "ingestion", thus the tablets are for absorption or action of the active agent in the gastrointestinal tract. Particular embodiments are coated tablets, layered tablets, laminated tablets, tablets with modified release of the active agent, matrix tablets, effervescent tablets, chewable tablets or pills. The formulations of the invention usually comprise at least a part of the necessary tablet excipients, such as binders, fillers, glidants and lubricants, and disintegrants. Tablets of formulations of the invention may also, if necessary, comprise other suitable excipients, for example excipients which assist tableting such as lubricants and glidants, e.g. magnesium, aluminum and calcium stearates, talc and silicones, animal or vegetable fats, especially in hydrogenated form and those which are solid at room temperature. Coated tablets additionally comprise suitable coating materials, for example film coating agents with coating aids, especially those mentioned below. Coated tablets include, in particular, sugar-coated tablets and film-coated tablets.

Powders are finely dispersed solids of formulations of the invention with particle sizes usually of less than 1 mm. The above statements about granules apply correspondingly.

The solid dispersion product described herein shows retarded release of the comprised active agent(s) into ambient aqueous media compared to solid dispersions which do not comprise polyvinyl alcohol-polyalkylene glycol graft copolymer(s) but instead an equal amount of the polymer(s) of N-vinyl lactams. Release of active agents from solid dispersion products may be determined according to chapter <711> Dissolution of United States Pharmacopeia (USP 33, 2010) using USP apparatus 2 (paddle) and 500 ml dissolution medium at a temperature of 37° C. and a stirring speed of 50 rpm. Dissolved active agent(s) may be detected by means of HPLC and UV/Vis photometry.

The release of 80% active agent(s) from a solid dispersion as described herein comprising 20% (w/w) polyvinyl alcohol-polyalkylene glycol graft copolymer(s), e.g. a polyvinyl alcohol-polyethylene glycol graft copolymer such as Kollicoat IR, may take at least 10%, for example at least 20%, at least 40%, at least 100%, and up to 200% longer than from a solid dispersion not comprising the polyvinyl alcohol-polyalkylene glycol graft copolymer(s) but an equal amount of the polymer(s) of N-vinyl lactams. The release of 80% active agent(s) from a solid dispersion as described herein comprising 40% (w/w) polyvinyl alcohol-polyalkylene glycol graft copolymer(s), e.g. a polyvinyl alcohol-polyethylene glycol graft copolymer such as Kollicoat IR, may take at least 50%, for example at least 100%, at least 150%, at least 200%, at least 300%, and up to 1000% longer than from a solid dispersion not comprising the polyvinyl alcohol-polyalkylene glycol graft copolymer(s) but an equal amount of the polymer(s) of N-vinyl lactams.

Using a mixture of the thermoplastic polymer(s) of N-vinyl lactams with the polyvinyl alcohol-polyalkylene glycol graft copolymer(s) allows to achieve a viscosity that can be adjusted.

EXAMPLES

Example 1

Preparation of Solid Dispersion Products

Solid dispersion products having compositions as indicated in Tables 1-3 were prepared as follows:

Blends of pharmaceutical compound, polymer(s) and excipient(s) were produced by dry mixing the ingredients given in TABLE 1 using a rotor lab mixer GT95 (Rotor Lips AG, Uetendorf, Switzerland). The ingredients were then molten and processed using a laboratory twin screw extruder (Haake PTW 16 mm, Thermo Scientific, Karlsruhe, Germany) equipped with a rod die (7 mm×13 mm) at an extrusion temperature of about 130° C. The melt rod was directly shaped into single dose units (lentils) of an approximate weight of 225 mg using a laboratory calendar.

TABLE 1

Composition of ibuprofen solid dispersion products

| Product # | Ibuprofen 38 [% (w/w)] | | PEG 1500 [% (w/w)] | Kollicoat IR* [% (w/w)] |
|---|---|---|---|---|
| | | Kollidon VA 64* [% (w/w)] | | |
| I-V-0 | 5 | 85 | 10 | 0 |
| I-V-20 | 5 | 65 | 10 | 20 |
| I-V-40 | 5 | 45 | 10 | 40 |
| | | Kollidon K17* [% (w/w)] | | |
| I-K-0 | 5 | 85 | 10 | 0 |
| I-K-20 | 5 | 65 | 10 | 20 |
| I-K-40 | 5 | 45 | 10 | 40 |

*available from BASF

TABLE 2

Composition of fenofibrate solid dispersion products

| Product # | Fenofibrate [% (w/w)] | | PEG 1500 [% (w/w)] | Kollicoat IR* [% (w/w)] |
|---|---|---|---|---|
| | | Kollidon VA 64* [% (w/w)] | | |
| F-V-0 | 5 | 85 | 10 | 0 |
| F-V-20 | 5 | 65 | 10 | 20 |
| F-V-40 | 5 | 45 | 10 | 40 |
| | | Kollidon K17* [% (w/w)] | | |
| F-K-0 | 5 | 85 | 10 | 0 |
| F-K-20 | 5 | 65 | 10 | 20 |
| F-K-40 | 5 | 45 | 10 | 40 |

*available from BASF

TABLE 3

Composition of paracetamol solid dispersion products

| Product # | Paracetamol [% (w/w)] | | PEG 1500 [% (w/w)] | Kollicoat IR* [% (w/w)] |
|---|---|---|---|---|
| | | Kollidon VA 64* [% (w/w)] | | |
| P-V-0 | 5 | 85 | 10 | 0 |
| P-V-20 | 5 | 65 | 10 | 20 |
| P-V-40 | 5 | 45 | 10 | 40 |
| | | Kollidon K17* [% (w/w)] | | |
| P-K-0 | 5 | 85 | 10 | 0 |
| P-K-20 | 5 | 65 | 10 | 20 |
| P-K-40 | 5 | 45 | 10 | 40 |

*available from BASF

Further, a reference solid dispersion product was prepared from the ingredients indicated in TABLE 4. The reference solid dispersion product was prepared as described above, however, the extrusion temperature had to be increased to about 180° C. in order to obtain a homogeneous melt.

TABLE 4

Composition of reference solid dispersion product

| Product # | Fenofibrate [% (w/w)] | PEG 1500 [% (w/w)] | Kollicoat IR* [% (w/w)] |
|---|---|---|---|
| F-85 | 5 | 10 | 85 |

Example 2

Analysis of Drug Release Characteristics of Solid Dispersion Products

The lentils of solid dispersion products prepared in example 1 were analyzed for drug release according to chapter <711> Dissolution of United States Pharmacopeia ($2^{nd}$ edition, 2008-2009). To this end, 0.7 g solid dispersion product was mixed with 500 ml dissolution medium (0.01 M HCl for solid dispersion products comprising paracetamol, phosphate buffer pH 7.2 for solid dispersion products comprising ibuprofen, 0.05 M SDS in $H_2O$ for solid dispersion products comprising fenofibrate) using USP apparatus 2 (paddle) at a temperature of 37° C. and a stirring speed of 50 rpm. Samples of 5 ml were taken 5, 10, 15, 20, 30, 45, 60, 90, 120 and 180 min after start of mixing. The amount of drug dissolved in the dissolution medium was determined by HPLC and UV/Vis photometry using a standard. Due to multiple sampling, volume correction was applied.

Figure 1:
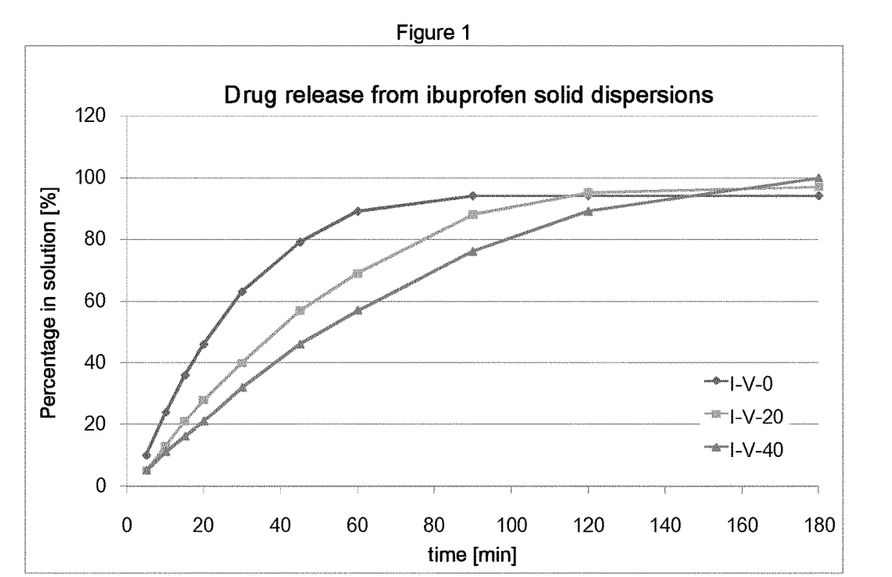
FIG. 1 shows release of ibuprofen from solid dispersion products comprising ibuprofen, Kollidon VA64 and varying percentages of Kollicoat IR.
Figure 2:
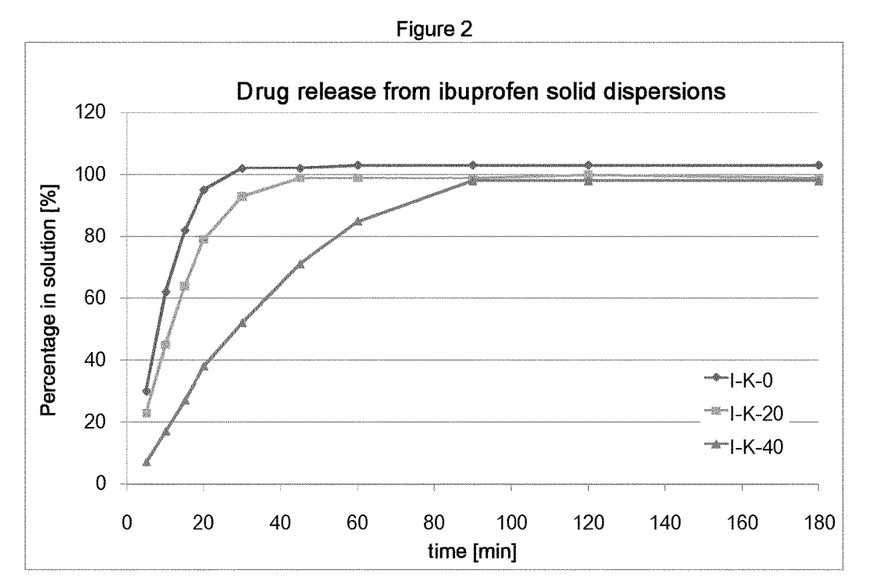
FIG. 2 shows release of ibuprofen from solid dispersion products comprising ibuprofen and Kollidon K17 and varying percentages of Kollicoat IR.
Figure 3:
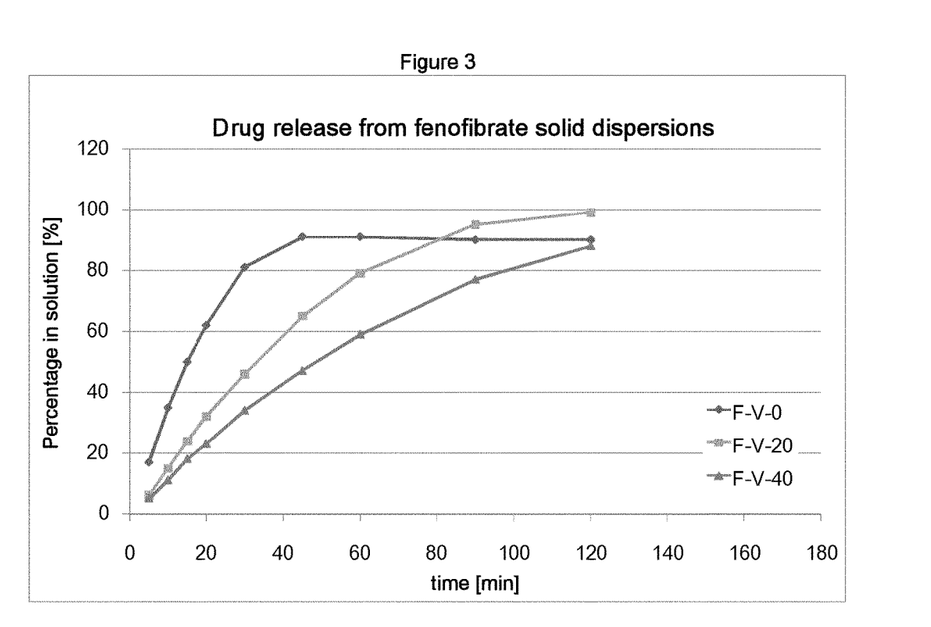
FIG. 3 shows release of fenofibrate from solid dispersion products comprising fenofibrate and Kollidon VA64 and varying percentages of Kollicoat IR.
Figure 4:
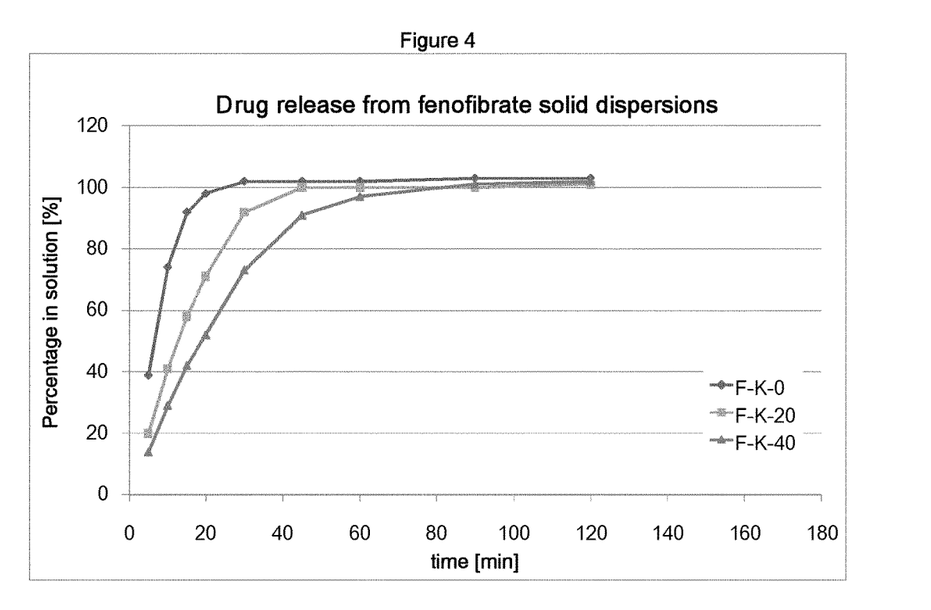
FIG. 4 shows release of fenofibrate from solid dispersion products comprising fenofibrate and Kollidon K17 and varying percentages of Kollicoat IR.
Figure 5:
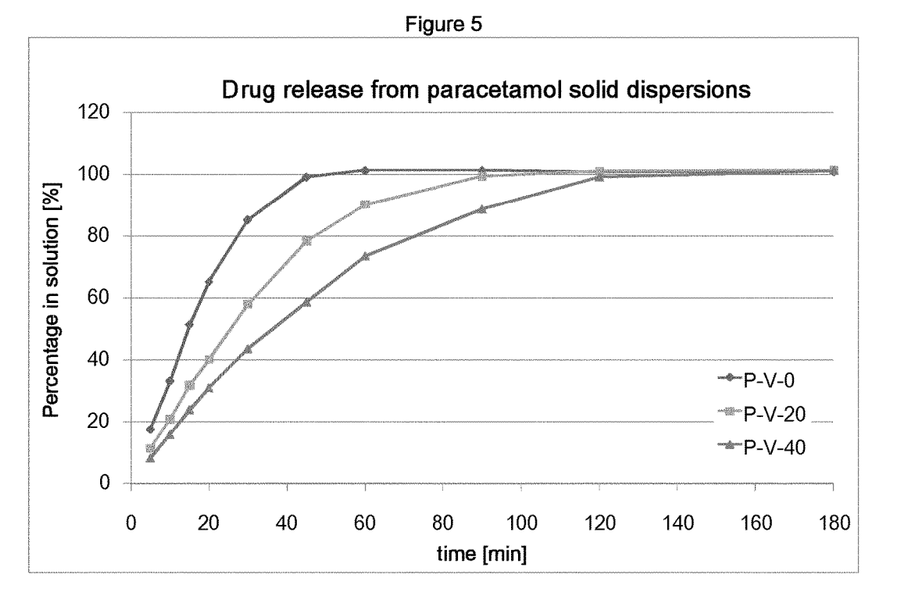
FIG. 5 shows release of paracetamol from solid dispersion products comprising paracetamol and Kollidon VA64 and varying percentages of Kollicoat IR.
Figure 6:
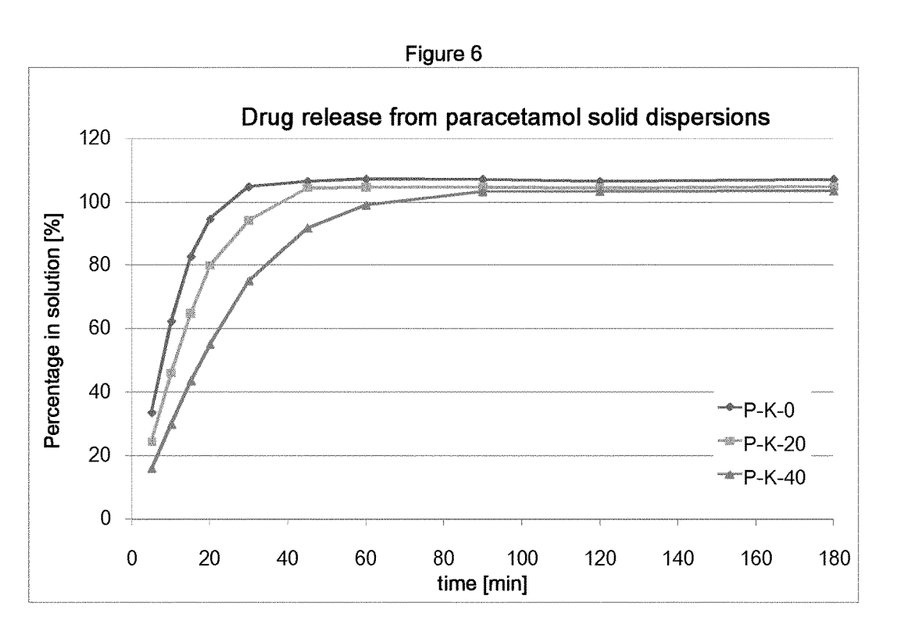
FIG. 6 shows release of paracetamol from solid dispersion products comprising paracetamol and Kollidon K17 and varying percentages of Kollicoat IR.

As illustrated in FIGS. 1 to 6, the release of the drugs ibuprofen, fenofibrate or paracetamol from the solid dispersion products, wherein an amount of the Kollidon equaling 20% (w/w) of the total weight of the product was replaced by Kollicoat IR, was significantly slower than from solid dispersions which did not comprise Kollicoat IR. The drug release rate was even lower from solid dispersion products, wherein an amount of the Kollidon equaling 40% (w/w) of the total weight of the product was replaced by Kollicoat IR.

Example 3

Analysis of Solid Dispersion Products by Raman Spectroscopy

Samples of the solid dispersion products prepared in example 1 were analyzed for residual drug crystallinity using a Raman microscope (type Aramis from Horiba). To this end, an extrudate lentil of the solid dispersion product to be analyzed was grinded to give a plane surface which was then examined by Raman spectroscopy. The resulting set of Raman spectra (one for each component of the solid dispersion product) was smoothed, normalized and baseline corrected, and used for establishing a model for assessment of homogeneity and distribution of the individual components. Results are shown in TABLE 5.

TABLE 5

Homogeneity and crystallinity of solid dispersion products

| Product # | Residual Drug crystallinity |
|---|---|
| I-V-40 | none |
| I-K-40 | none |
| F-V-40 | none |
| F-K-40 | low |
| F-85 | high |

The invention claimed is:

1. A formulation comprising a melt-processed solid dispersion product comprising, relative to the total weight of the product:
    (a) one or more active agents;
    (b) 10 to 90% (w/w) of at least one pharmaceutically acceptable thermoplastic polymer of N-vinyl lactams; and
    (c) 20 to 60% (w/w) of at least one pharmaceutically acceptable polyvinyl alcohol-polyalkylene glycol graft copolymer
    wherein the active agent(s) is/are present in a non-crystalline state, said state being characterized in that a differential scanning calorimetry (DSC) measurement lacks the melting peak which occurs in a DSC measurement with a crystalline substance of the active agent(s), and
    wherein the weight ratio of the polyvinyl alcohol-polyalkylene glycol graft copolymer(s) to the thermoplastic polymer(s) of N-vinyl lactams is from about 1:1 to about 1:8.

2. The formulation of claim 1, wherein the solid dispersion product further comprises 5 to 20% (w/w) of at least one plasticizer.

3. The formulation of claim 2, wherein the plasticizer is a polyethylene glycol having a number average molecular weight of from 600 to 6,000 Daltons.

4. The formulation of any one of claims 1 to 3, wherein the pharmaceutically acceptable graft copolymer comprises vinyl alcohol polymer chains having the structure:

wherein n is from 250 to 1000
and of a polyalkylene glycol chain having the structure:

wherein m is from 100 to 500.

5. The formulation of claim 1, wherein the at least one pharmaceutically acceptable thermoplastic polymer of N-vinyl lactams is selected from homopolymers and copolymers of N-vinyl pyrrolidone.

6. The formulation of claim 1, wherein the at least one pharmaceutically acceptable thermoplastic polymer of N-vinyl lactams is selected from copolymers of N-vinyl pyrrolidone and vinyl acetate or vinyl propionate.

7. The formulation of claim 1, wherein the active agent is selected from the group consisting of ibuprofen, fenofibrate, and paracetamol.

8. A method for preparing the formulation of claim 1, comprising:
    (a) blending one or more active agents; 10 to 90% (w/w) of at least one pharmaceutically acceptable thermoplastic polymer of N-vinyl lactams; and 20 to 60% (w/w) of at least one pharmaceutically acceptable polyvinyl alcohol-polyalkylene glycol graft copolymer; relative to the total weight of the mixture;
    (b) heating the blend to obtain a homogeneous melt;
    (c) forcing the thus obtained melt through one or more nozzles; and
    (d) allowing the melt to solidify to obtain a solid dispersion product.

9. The method of claim 8, wherein step (b) is carried out in an extruder and the blend is subjected to a mixing action in a mixing section of the extruder.

10. A formulation comprising a melt-processed solid dispersion product comprising, relative to the total weight of the product:
    (a) one or more active agents;
    (b) 10 to 90% (w/w) of at least one pharmaceutically acceptable thermoplastic copolymer of N-vinyl pyrrolidone and N-vinyl acetate or a copolymer of N-vinyl pyrrolidone and vinyl propionate;
    (c) 5 to 60% (w/w) of at least one pharmaceutically acceptable polyvinyl alcohol-polyalkylene glycol graft copolymer; and
    (d) optionally up to 20% (w/w) of at least one plasticizer;
    wherein the active agent(s) is/are present in a non-crystalline state, said state being characterized in that a differential scanning calorimetry (DSC) measurement lacks the melting peak which occurs in a DSC measurement with a crystalline substance of the active agent(s), and
    wherein the weight ratio of the polyvinyl alcohol-polyalkylene glycol graft copolymer(s) to the thermoplastic polymer(s) of N-vinyl lactams is from about 1:1 to about 1:8.

11. A formulation comprising a melt-processed solid dispersion product comprising, relative to the total weight of the product:
    (a) one or more active agents;
    (b) 10 to 90% (w/w) of at least one pharmaceutically acceptable thermoplastic homopolymer of N-vinyl pyrrolidone;
    (c) 5 to 60% (w/w) of at least one pharmaceutically acceptable polyvinyl alcohol-polyalkylene glycol graft copolymer; and
    (d) optionally up to 20% (w/w) of at least one plasticizer;
    wherein the active agent(s) is/are present in a non-crystalline state, said state being characterized in that a differential scanning calorimetry (DSC) measurement lacks the melting peak which occurs in a DSC measurement with a crystalline substance of the active agent(s), and
    wherein the weight ratio of the polyvinyl alcohol-polyalkylene glycol graft copolymer(s) to the thermoplastic polymer(s) of N-vinyl lactams is from about 1:1 to about 1:8.

12. The formulation of claim 10, comprising a melt-processed solid dispersion product consisting essentially of, relative to the total weight of the product:

(a) one or more active agents;
(b) 10 to 90% (w/w) of at least one pharmaceutically acceptable thermoplastic copolymer of N-vinyl pyrrolidone and N-vinyl acetate or a copolymer of N-vinyl pyrrolidone and vinyl propionate;
(c) 5 to 60% (w/w) of at least one pharmaceutically acceptable polyvinyl alcohol-polyalkylene glycol graft copolymer; and
(d) optionally up to 20% (w/w) of at least one plasticizer;
wherein the active agent(s) is/are present in a non-crystalline state, said state being characterized in that a differential scanning calorimetry (DSC) measurement lacks the melting peak which occurs in a DSC measurement with a crystalline substance of the active agent(s), and
wherein the weight ratio of the polyvinyl alcohol-polyalkylene glycol graft copolymer(s) to the thermoplastic polymer(s) of N-vinyl lactams is from about 1:1 to about 1:8.

13. The formulation of claim 11, comprising a melt-processed solid dispersion product consisting essentially of, relative to the total weight of the product:

(a) one or more active agents;
(b) 10 to 90% (w/w) of at least one pharmaceutically acceptable thermoplastic homopolymer of N-vinyl pyrrolidone;
(c) 5 to 60% (w/w) of at least one pharmaceutically acceptable polyvinyl alcohol-polyalkylene glycol graft copolymer; and
(d) optionally up to 20% (w/w) of at least one plasticizer;
wherein the active agent(s) is/are present in a non-crystalline state, said state being characterized in that a differential scanning calorimetry (DSC) measurement lacks the melting peak which occurs in a DSC measurement with a crystalline substance of the active agent(s), and
wherein the weight ratio of the polyvinyl alcohol-polyalkylene glycol graft copolymer(s) to the thermoplastic polymer(s) of N-vinyl lactams is from about 1:1 to about 1:8.

* * * * *